(12) United States Patent
Heggendorn et al.

(10) Patent No.: US 8,992,626 B2
(45) Date of Patent: Mar. 31, 2015

(54) KNEE PROSTHESIS WITH GUIDED EXTENSION AND FLEXION

(75) Inventors: Marco A. H. Heggendorn, Pura (CH); Roger Scherrer, Schallhauser (CH); Matthias Schapper, Winterthur (CH)

(73) Assignee: Zimmer GmbH, Winterthur (CH)

( * ) Notice: Subject to any disclaimer, the term of this patent is extended or adjusted under 35 U.S.C. 154(b) by 0 days.

(21) Appl. No.: 13/884,915

(22) PCT Filed: Nov. 10, 2011

(86) PCT No.: PCT/EP2011/069842
§ 371 (c)(1),
(2), (4) Date: Sep. 30, 2013

(87) PCT Pub. No.: WO2012/062856
PCT Pub. Date: May 18, 2012

(65) Prior Publication Data
US 2014/0018929 A1     Jan. 16, 2014

Related U.S. Application Data

(60) Provisional application No. 61/413,085, filed on Nov. 12, 2010.

(51) Int. Cl.
*A61F 2/38* (2006.01)
*A61F 2/30* (2006.01)

(52) U.S. Cl.
CPC .............. *A61F 2/3886* (2013.01); *A61F 2/3868* (2013.01); *A61F 2002/30332* (2013.01); *A61F 2002/30604* (2013.01); *A61F 2002/30878* (2013.01)
USPC ....................................................... 623/20.27

(58) Field of Classification Search
USPC .......... 623/20.14, 20.15, 20.21, 20.27, 20.28, 623/20.31
See application file for complete search history.

(56) References Cited

U.S. PATENT DOCUMENTS

2006/0265080 A1* 11/2006 McMinn ..................... 623/20.27

FOREIGN PATENT DOCUMENTS

EP        1133959 A1     3/2001
(Continued)

OTHER PUBLICATIONS

"International Application Serial No. PCT/EP2011/069842, International Preliminary Report on Patentability mailed Dec. 21, 2012", 6 pgs.
"International Application Serial No. PCT/EP2011/069842, International Search Report mailed Feb. 6, 2012", 5 pgs.

(Continued)

*Primary Examiner* — Howie Matthews
(74) *Attorney, Agent, or Firm* — Schwegman Lundberg & Woessner, P.A.

(57) ABSTRACT

An orthopaedic knee joint prosthesis (10) provides guided motion in a wide range of motion, and in both extension and flexion. In flexion, a tibial bearing component (16) shifts to a first position in which a posterior cam (36) formed in a femoral component (12) engages a tibial spine (18) coupled to a tibial component (14). Contact between the posterior cam and the spine guides the motion profile of the knee joint prosthesis throughout a wide range of flexion movement. In extension, the bearing component shifts to a second position in which an anterior cam (34) formed in the femoral component engages the spine. Contact between the anterior cam and spine guides the motion profile of the knee joint prosthesis throughout a wide range of extension. The anterior and posterior cams, mobile bearing component, and tibial component-mounted spine cooperate to facilitate guided flexion and extension of the knee joint prosthesis throughout a wide range of motion.

17 Claims, 4 Drawing Sheets

(56) References Cited

FOREIGN PATENT DOCUMENTS

| | | | |
|---|---|---|---|
| EP | 1378216 | A2 | 1/2004 |
| FR | 2844704 | A1 | 3/2004 |
| WO | WO-2004058108 | A1 | 7/2004 |
| WO | WO-2012062856 | A1 | 5/2012 |

OTHER PUBLICATIONS

"International Application Serial No. PCT/EP2011/069842, Written Opinion mailed Feb. 6, 2012", 6 pgs.

"International Application Serial No. PCT/EP2011/069842, Demand and Letter filed Sep. 12, 2012", 10 pgs.

* cited by examiner

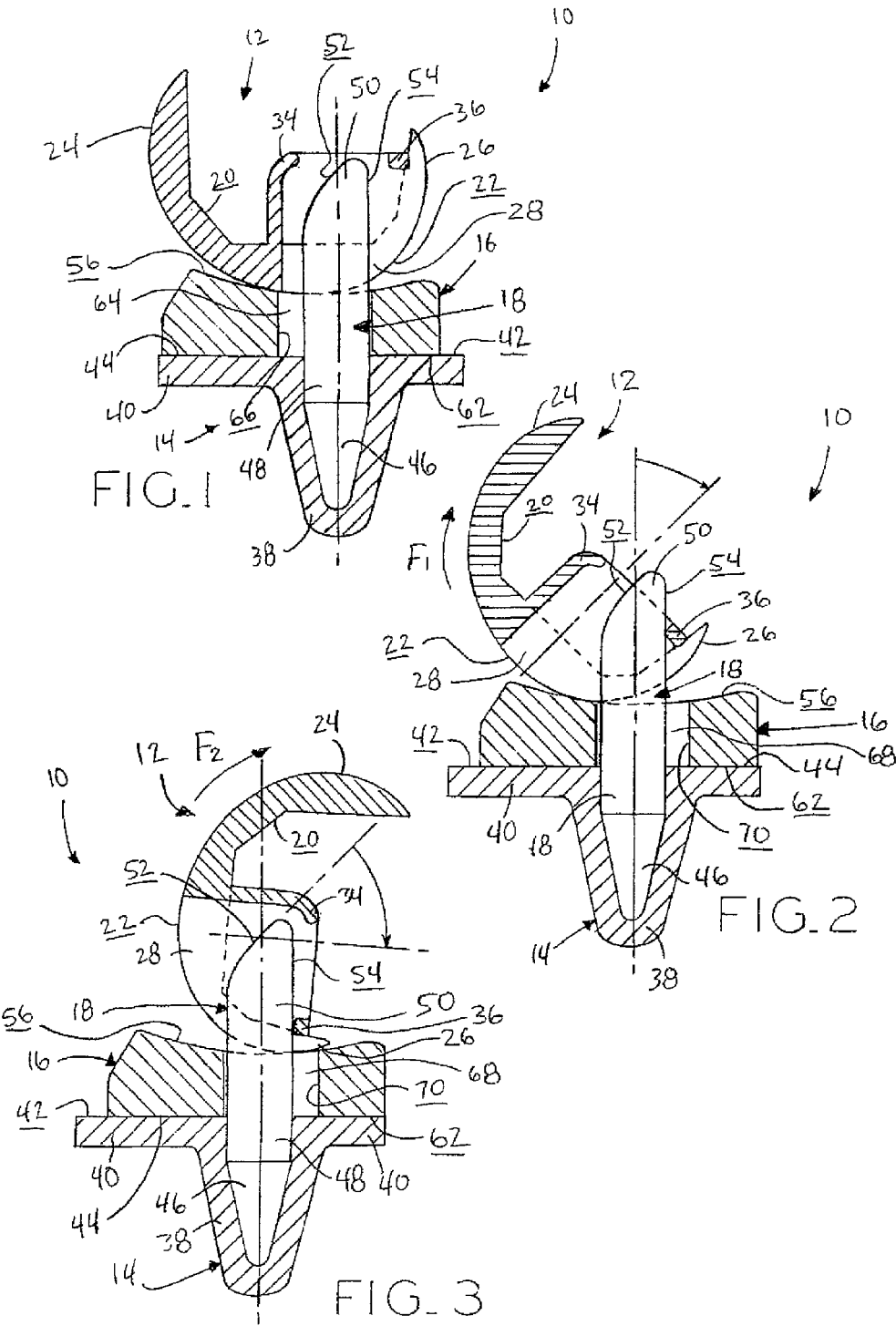

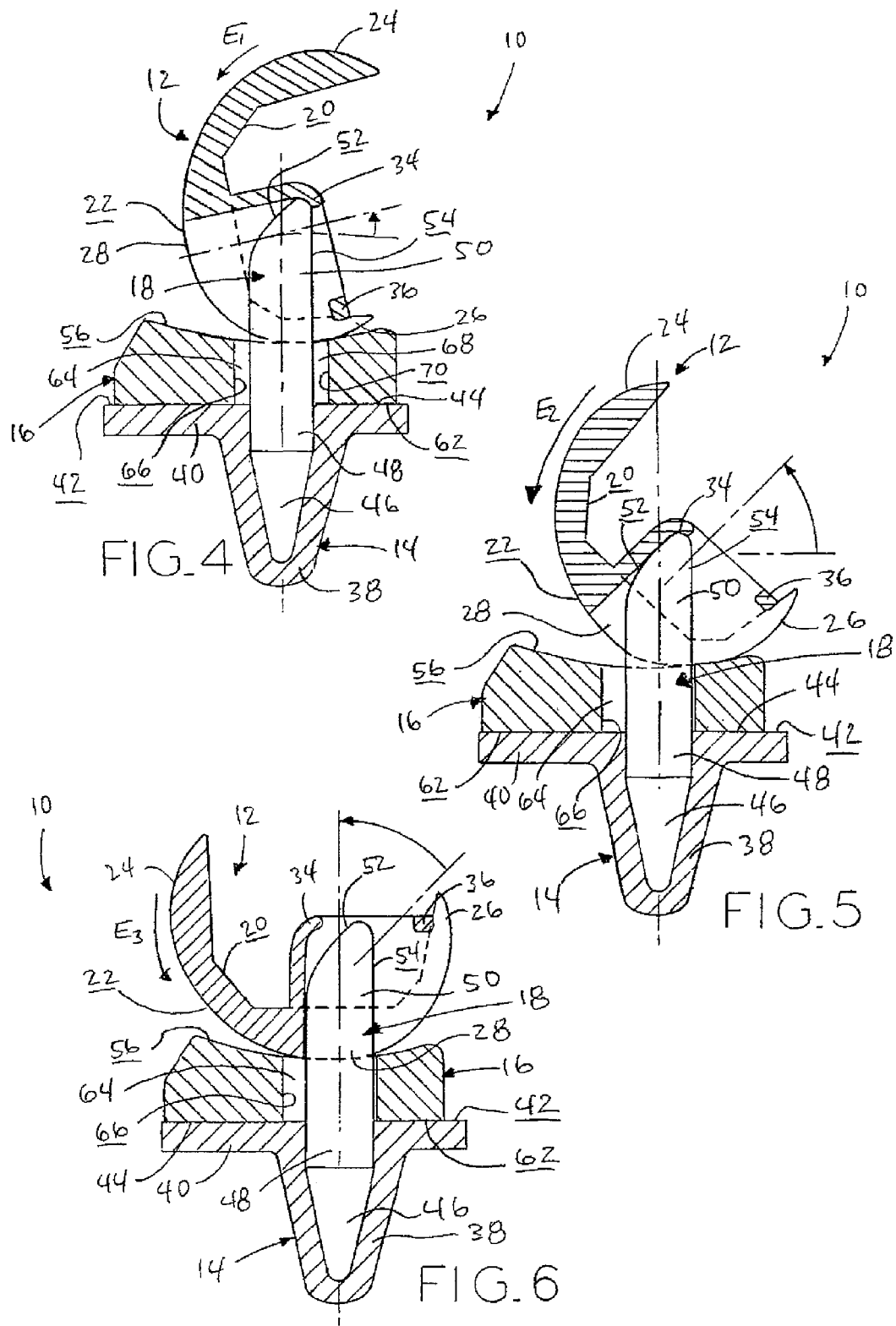

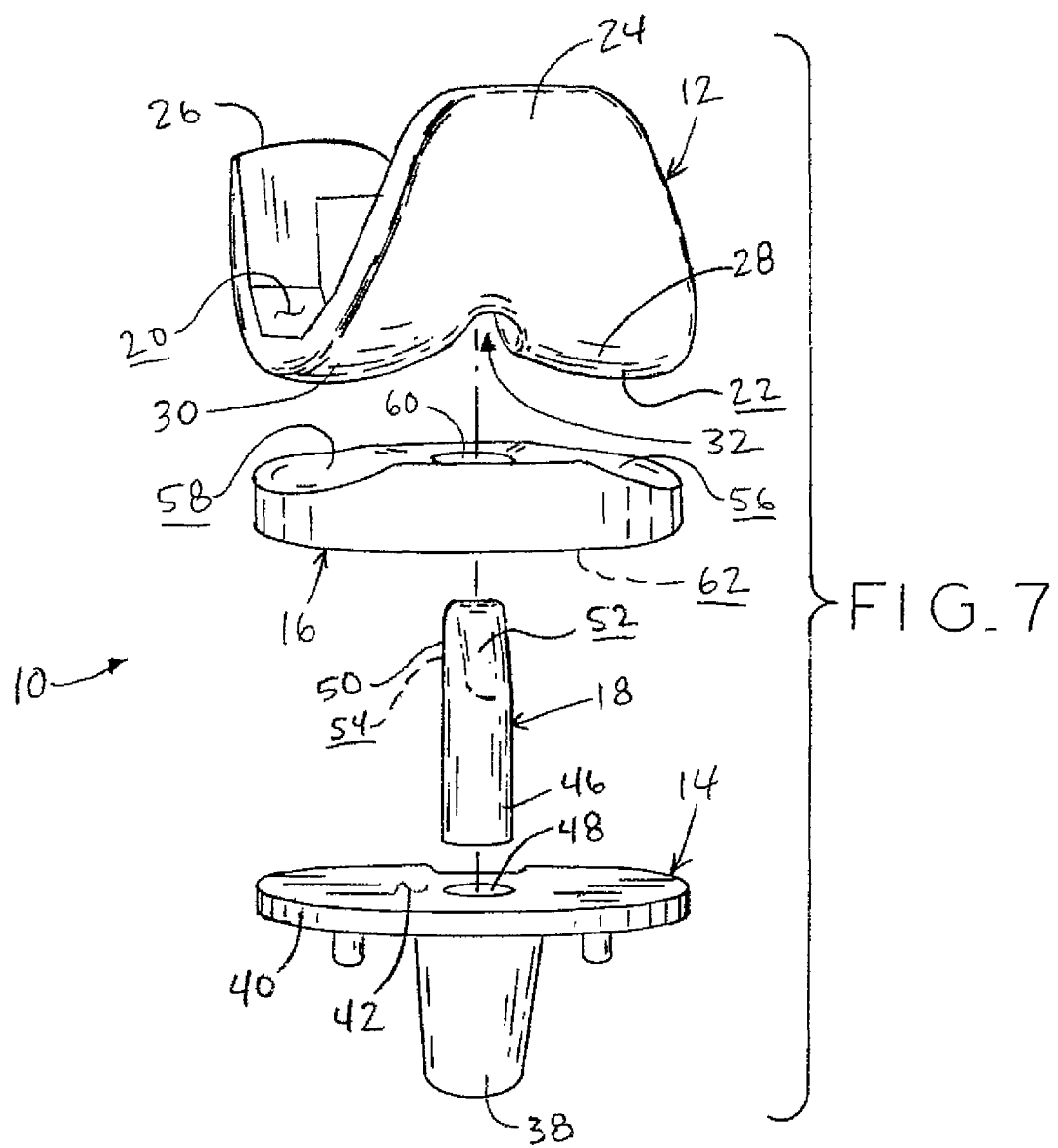

KNEE PROSTHESIS WITH GUIDED EXTENSION AND FLEXION

CLAIM OF PRIORITY

This application is a U.S. National Stage Filing under 35 U.S.C. 371 of International Application No. PCT/EP2011/069842, filed on Nov. 10, 2011, and published as WO 2012/062856 A1 on May 18, 2012, which claims the benefit of U.S. Provisional Application Ser. No. 61/413,085, filed on Nov. 12, 2010, both of which are hereby incorporated herein by reference in their entireties.

BACKGROUND

1. Technical Field

The present disclosure relates to orthopaedic prostheses and, specifically, to knee prostheses.

2. Description of the Related Art

Orthopaedic prostheses are commonly utilized to repair and/or replace damaged bone and tissue in the human body. For example, a knee prosthesis may include a tibial component and/or a femoral component to replace damaged and/or destroyed bone in the tibia and/or femur. Knee prostheses seek to provide articulation similar to the natural, anatomical articulation of the knee joint.

Total knee replacement (TKR) surgery involves the implantation of several components meant to restore the functionality normally provided by a natural knee. Typical TKR components include a tibial component, a femoral component, and an insert or bearing component disposed between the tibial and femoral components. The insert component is used to provide an appropriate level of friction and contact area at the interface between the femoral component and the insert. For example, a high degree of conformity between the convex curvature of the femoral component and the corresponding concave curvature of the tibial insert results in a large area of contact and correspondingly low pressure at the interface. However, this high degree of conformity also increases the magnitude of shear forces between the femoral component and insert during articulation between the insert and femoral component, i.e., during flexion and extension of the knee.

In certain TKR prostheses, which may be referred to as "posterior stabilized" prostheses, a cam positioned at the posterior portion of the intercondylar fossa of a femoral component cooperates with a spine formed in a tibial component to guide or constrain motion within certain predefined boundaries. For example, posterior stabilized prostheses may include a spine integrally formed with a tibial bearing insert (or "meniscal component") which interacts with a cam formed in a femoral component to promote femoral roll back during flexion of the TKR prosthesis. Typically, the articular interface between the femoral component and tibial insert is of low- or medium-congruency to facilitate the sliding motion which occurs during femoral rollback. Posterior stabilized prostheses are appropriate where the posterior cruciate ligament (PCL) is torn or otherwise damaged, or where the PCL is resected during surgery.

In addition, some knee prostheses include posterior-facing structures within a femoral component which engage an anterior-facing surface of the tibial spine when the knee prosthesis is in a "full extension" or "hyperextension" configuration. In these systems, interaction between the femoral component and spine operates as a physical stop against extension of the knee prosthesis past a predetermined level of extension. Such "hyperextension stops" typically result in full engagement of the femoral component and tibial spine at a single point of extension or hyperextension, or within a narrow range of extension or hyperextension, as opposed to engaging throughout a range of motion.

On the other hand, some femoral components interact with a tibial spine over a range of knee prosthesis motion in order to facilitate a particular motion profile throughout a "guided" range of motion. In some instances, for example, interaction between a femoral component structure and a tibial spine may be used to mimic a natural motion profile within certain motion ranges. One such motion profile, for example, might mimic external rotation of the femoral component in deep flexion. A guided motion profile may also mimic "femoral roll back", i.e., the posterior translation of the femoral/tibial articulation contact point during flexion.

In still other TKR knee prosthesis designs, a tibial insert may be allowed to move within a limited range of motion upon the proximal tibial plate of the tibial component. In these "mobile bearing" knee prosthesis systems, translation of the femoral component relative to the tibial component may be accomplished by movement at the interface between the tibial insert and the tibial plate, rather than at the interface between the tibial insert and the femoral condyle.

SUMMARY

The present disclosure provides an orthopaedic knee joint prosthesis which provides guided motion throughout a wide range of motion, in both extension and flexion. When the prosthesis is flexed (i.e., the knee is bent), a tibial bearing component shifts to a first position in which a posterior cam formed in a femoral component engages a tibial spine coupled to a tibial component. When so engaged, contact between the posterior cam and the spine guides the motion profile of the knee joint prosthesis throughout a wide range of flexion movement. When the prosthesis is extended (i.e., the knee is straightened from a flexed position), the bearing component shifts to a second position in which an anterior cam formed in the femoral component engages the spine. When so engaged, the anterior cam and spine guide the motion profile of the knee joint prosthesis throughout a wide range of extension movement. The anterior and posterior cams, mobile bearing insert, and tibial component-mounted spine all cooperate to facilitate guided flexion and extension of the knee joint prosthesis throughout a wide range of motion.

While the anterior cam engages the spine when a posteriorly-directed force is acting on the femoral component with respect to the tibial component, e.g. when the prosthesis moves from flexion to extension, the posterior cam engages the spine when an anteriorly-directed force is acting on the femoral component with respect to the tibial component, e.g. when the prosthesis moves from extension to flexion.

To facilitate the wide range of extension and flexion guidance, the mobile bearing component allows the anterior and posterior cams to translate relative to the spine. This translation occurs during the inflection from flexion to extension motions, or vice versa, which changes the position of the bearing insert and toggles between anterior cam/spine interaction and posterior cam/spine interaction.

In one form thereof, the present invention provides a knee joint prosthesis movable between extension and flexion, the prosthesis comprising: a femoral component comprising: a lateral condyle and a medial condyle; an articular surface including respective surfaces of the lateral and medial condyles; a bone-contacting surface opposite the articular surface, the bone-contacting surface adapted to abut a distal portion of a femur when the femoral component is affixed to the femur; an anterior cam; and a posterior cam disposed posterior of the anterior cam; a tibial component having a tibial plate with a spine extending proximally therefrom, the anterior cam engageable with the spine to create a first transverse force as the femoral component is moved through a range of prosthesis motion from a flexion configuration to an extension configuration, the tibial plate defining a proximally-facing tibial component bearing surface; and a tibial insert comprising: a distal insert bearing surface slidably abutting the tibial component bearing surface to define an interface therebetween, the interface providing a first resistance to transverse movement for a given compression between the tibial insert and the tibial component applied at the interface; and a proximal articular surface sized and shaped to abut the lateral condyle and the medial condyle of the femoral component to provide a second resistance to transverse movement for the given compression, the second resistance greater than the first resistance, the first transverse force greater than the first resistance to movement, whereby the femoral component and the tibial insert translate as a pair when the anterior cam engages the spine.

In another form thereof, the present invention provides a knee joint prosthesis, comprising: a tibial component having a proximally-facing tibial plate; a spine coupled to the tibial component and protruding proximally from the tibial plate, the spine defining an anteroposterior span; a tibial insert attachable to the tibial component, the tibial insert comprising: an insert bearing surface in abutting, sliding engagement with the tibial plate of the tibial component; a proximal articulation surface, the articulation surface positioned opposite the insert bearing surface; and an oblong aperture formed within the tibial insert so that at least a portion of the spine passes through the oblong aperture, the oblong aperture having an anteroposterior extent larger than the anteroposterior span of the spine, whereby the tibial insert is slidable in an anteroposterior direction with respect to the tibial component; and a femoral component articulable with the tibial insert between an extension configuration and a flexion configuration, the femoral component comprising: an articular surface abutting the articulation surface of the tibial insert when the femoral component articulates with the tibial insert; an anterior cam engageable with the spine through a first range of motion from the flexion configuration to the extension configuration; and a posterior cam engageable with the spine through a second range of motion from the extension configuration to the flexion configuration.

In yet another form thereof, the present invention provides a knee joint prosthesis, comprising: a femoral component comprising: a lateral condyle and a medial condyle; an articular surface including respective surfaces of the lateral and medial condyles; a bone-contacting surface opposite the articular surface, the bone-contacting surface adapted to abut a distal portion of a femur when the femoral component is affixed to the femur; an anterior cam; and a posterior cam disposed posterior of the anterior cam; a tibial component having a tibial plate with a spine extending proximally therefrom, the tibial plate defining a proximally-facing tibial component bearing surface; a tibial insert comprising: a distal insert bearing surface slidably abutting the tibial component to define an interface therebetween, the interface providing a first resistance to transverse movement for a given compression between the tibial insert and the tibial component applied at the interface; and a proximal articular surface sized and shaped to abut the lateral condyle and the medial condyle of the femoral component to provide a second resistance to transverse movement for the given compression, the second resistance greater than the first resistance; and means for anteroposteriorly shifting the tibial insert and the femoral component with respect to the tibial component when a prosthesis inflection between extension and flexion movements occurs.

The means for anteroposteriorly shifting may operate to disengage one of said posterior cam and said anterior cam from said spine and engage the other of said posterior cam and said anterior cam with said spine when the prosthesis inflection occurs.

The means for anteroposteriorly shifting may comprise said articular surface of said femoral component in cooperation with a proximal articulation surface of said tibial insert, and said interface.

The means for anteroposteriorly shifting may include an oblong aperture formed in said tibial insert, said oblong aperture defining an anteroposterior span that is greater than a corresponding anteroposterior span of said spine.

BRIEF DESCRIPTION OF THE DRAWINGS

The above mentioned and other features and advantages of this invention, and the manner of attaining them, will become more apparent and the invention itself will be better understood by reference to the following description of an embodiment of the invention taken in conjunction with the accompanying drawings, wherein:

FIG. 1 is an elevation, cross-section view of a knee joint prosthesis in accordance with the present disclosure, shown in an extension configuration as a flexion motion is initiated;

FIG. 2 is an elevation, section view of the knee joint prosthesis shown in FIG. 1, shown in a partial flexion configuration during a flexion motion;

FIG. 3 is an elevation, partial section view of the knee joint prosthesis shown in FIG. 1, shown in a high flexion configuration during a flexion motion;

FIG. 4 is an elevation, partial section view of the knee joint prosthesis shown in FIG. 1, shown in a slightly less flexed configuration than is shown in FIG. 3, after an inflection from flexion to extension motion;

FIG. 5 is an elevation, partial section view of the knee joint prosthesis shown in FIG. 1, in a partial flexion configuration during an extension motion;

FIG. 6 is an elevation, section view of the knee joint prosthesis shown in FIG. 1 in an extended configuration after an extension motion;

FIG. 7 is a perspective, exploded view of a knee joint prosthesis in accordance with the present disclosure.

Corresponding reference characters indicate corresponding parts throughout the several views. The exemplification set out herein illustrates an exemplary embodiment of the invention, and such exemplification is not to be construed as limiting the scope of the invention in any manner.

DETAILED DESCRIPTION

Figure 8:
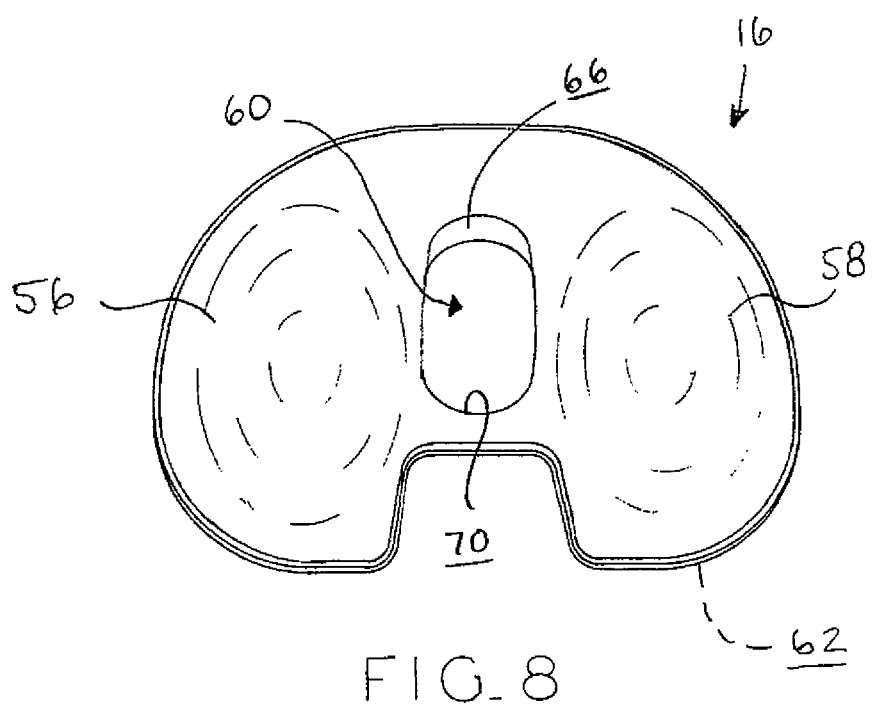
FIG. 8 is a perspective view of a tibial insert in accordance with the present disclosure.

The present disclosure provides a knee joint prosthesis which enables guided flexion and extension movement, via cam/spine interaction, throughout a wide range of both flexion and extension motions. The knee joint prosthesis includes a tibial component, a tibial insert component that is movable with respect to the tibial component (i.e., a "mobile bearing" tibial insert), a spine extending proximally from the tibial component and through the tibial insert, and a femoral component having a pair of cams which interact with the spine. More particularly, a knee joint prosthesis of the present disclosure guides a wide range of flexion motion, with the flexion guidance driven by interaction between a posterior cam and the spine. Conversely, a wide range of extension motion is guided by interaction between an anterior cam and the spine. The mobile bearing platform facilitates toggling between anterior cam/spine contact and posterior cam/spine contact.

Advantageously, a knee joint prosthesis in accordance with the present disclosure achieves low contact pressures resulting from high conformity between the femoral component and tibial insert, while also achieving low wear and high longevity from the mobile bearing. In addition, the guided motion in extension and flexion enable substantial control over the motion profile of the knee joint prosthesis.

In order to prepare the tibia and femur for receipt of a knee joint prosthesis of the present disclosure, any suitable methods or apparatuses for preparation of the knee joint may be used. In the following discussion, "proximal" refers to a direction toward the torso of a patient, while "distal" refers to the opposite direction of proximal, i.e., away from the torso of the patient. "Anterior" refers to a direction toward the front of a patient, while "posterior" refers to the opposite direction of anterior, i.e., toward the back of the patient. With respect to knee prosthesis components, "anterior," "posterior," "proximal" and "distal" refer to the orientation of the components with respect to the patient when the knee prosthesis is in an extension configuration (i.e., corresponding to a straight leg). While the embodiment described herein is described with regard to a right knee, it will be appreciated that the present disclosure is equally applicable to a left knee configuration.

1. Knee Joint Prosthesis Construction

Referring now to FIG. 1, knee joint prosthesis 10 includes femoral component 12, tibial component 14, tibial insert 16 and spine 18. Femoral and tibial components 12, 14 are adapted to mount to a distal femur and a proximal tibia, respectively, as discussed in detail below. Tibial insert 16 abuts a proximal surface of tibial component 14 and is disposed between femoral component 12 and tibial component 14. Femoral component 12 is received upon tibial insert 16, and tibial insert 16 provides bearing surfaces between femoral and tibial components 12, 14 during articulation of knee joint prosthesis 10. Spine 18 is coupled to tibial component 14 and extends proximally through tibial insert 16 and into engagement with femoral component 12.

As best seen in FIG. 7, femoral component 12 includes bone contacting surface 20 and articular surface 22, each extending between anterior side 24 and posterior side 26 of femoral component 12. Bone contacting surface 20 is adapted to affix femoral component 12 to a distal portion of a femur, such as with bone cement. Femoral component 12 includes medial condyle 28 and lateral condyle 30, with intercondylar fossa 32 formed between condyles 28, 30. Articular surface 22 is disposed generally opposite bone contacting surface 20, and is comprised of the exterior surface of both medial condyle 28 and lateral condyle 30 as well as the exterior surface of the anterior flange of femoral component 12. Anterior cam 34 extends proximally (i.e., upwardly) from bone contacting surface 20 proximate anterior side 24, and, in the exemplary embodiment, is near the anterior end of intercondylar fossa 32 (i.e., near the point on anterior side 24 of femoral component 12 where intercondylar fossa 32 terminates). Femoral component 12 further includes posterior cam 36 proximate posterior side 26 and between medial and lateral condyles 28, 30. Posterior cam 36 is located posterior of anterior cam 34, and spans intercondylar fossa 32 from medial condyle 28 to lateral condyle 30. As will be described in more detail below, anterior and posterior cams 34, 36 cooperate with spine 18 to guide flexion and extension motions, respectively, of knee joint prosthesis 10.

Referring still to FIG. 7, tibial component 14 includes tibial stem 38 extending distally from tibial plate 40 and away from tibial insert 16. Tibial stem 38 is adapted to be received within the intramedullary canal of a tibia to anchor tibial component 14 to the proximal end of the tibia. Tibial plate 40 further includes a proximally-facing tibial component bearing surface 42. As will be described in more detail below, tibial component bearing surface 42 is adapted to allow low friction sliding motion between tibial insert 16 and tibial component 14 at interface 44 (FIGS. 1-6), so that tibial insert 16 and femoral component 12 move together as a pair. Stated another way, tibial insert 16 and femoral component 12 are adapted to translate as a single unit with respect to tibial component 14, under certain articular conditions and within certain ranges of flexion of knee prosthesis 10, as discussed in detail below.

As best seen in FIGS. 1-6, spine 18 extends proximally from bearing surface 42 of tibial plate 40. In the illustrated embodiment, spine 18 is shown as a separate component including distal spine portion 46, which is sized to be received within a correspondingly sized cavity 48 (FIG. 7) formed in tibial component 14. In one embodiment of the present disclosure, distal spine portion 46 may be generally cylindrical in shape. In other embodiments, distal spine portion 46 of spine 18 may be non-cylindrical in shape and may be fixedly captured within tibial component 14. In still another alternative embodiment, spine 18 may be integrally and/or monolithically formed with tibial component 14. Proximal portion 50 of spine 18 defines anterior cam surface 52 and posterior cam surface 54. As described in detail below, anterior cam surface 52 is shaped and adapted to cooperate with anterior cam 34 of femoral component 12 to guide knee joint prosthesis 10 as the leg is straightened, thereby generating desired articular characteristics during extension. Similarly, posterior cam surface 54 is shaped and adapted to cooperate with posterior cam 36 to guide knee joint prosthesis 10 as the leg is bent, thereby generating desired articular characteristics during flexion.

Referring back to FIG. 7, the proximal, upwardly-facing surface of tibial insert 16 includes medial articulation surface 56 and lateral articulation surface 58, which are shaped to articulate with medial condyle 28 and lateral condyle 30, respectively. Tibial insert 16 also includes distal bearing surface 62 disposed opposite articulation surfaces 56, 58. When placed in abutting, slidable engagement with tibial component bearing surface 42, distal bearing surface 62 cooperates with tibial component bearing surface 42 to provide low friction interface 44.

Medial and lateral articulation surfaces 56, 58 have a high congruence with articular surface 22 of femoral component 12, in that the convex curvature of medial and lateral condyles 28, 30 closely corresponds to the concave curvature of medial and lateral articulation surfaces 56, 58, respectively. As described in detail below, this high congruence maintains a large area of contact between the respective articular surfaces of femoral component 12 and tibial insert 16, while also increasing the capacity for transfer of transverse forces from femoral component 12 to tibial insert 16. For purposes of the present disclosure, transverse forces are forces having a medial/lateral vector component, an anterior/posterior vector component, or a combination thereof. For a standing or walking patient, transverse forces are generally parallel to the anatomic transverse plane of the body.

Transverse forces acting at articular contact areas between femoral component 12 and tibial insert 16 may be generated, for example, by interaction between anterior and/or posterior cams 34, 36 of femoral component 12 and spine 18. For example, when anterior cam 34 comes into contact with anterior cam surface 52 of proximal spine portion 50 during extension (as described in detail below), a transverse force acts on femoral component 12 by the (stationary) spine 18 which tends to urge femoral component 12 anteriorly. Conversely, when posterior cam 36 comes into contact with posterior cam surface 54 of proximal spine portion 50 during flexion, a transverse force acts on femoral component 12 by spine 18 which tends to urge femoral component 12 posteriorly.

The high surface congruence at the interface of articular surface 22 of femoral component 12 and articulation surfaces 56, 58 of tibial insert 16 increases the potential for the two components to withstand relatively high shear forces during articulation of prosthesis 10 without sliding relative to one another. The concave, dished contour of articulation surfaces 56, 58 cradle to the correspondingly convex contour of respective condyles 28, 30, such that femoral component 12 would have to move proximally (or tibial insert 16 would have to move distally) to accommodate a relative sliding motion therebetween. In this way, the congruence at the articular interface between femoral component 12 and tibial insert 16 presents a physical barrier to transverse movement (e.g., anteroposterior translation).

On the other hand, the relatively low-friction interface 44 between tibial insert 16 and tibial component 14 creates a differential in resistance to sliding upon application of a transverse force, with the lower interface 44 allowing sliding motion at a lower force threshold. As a result of this differential, transverse forces generated in femoral component 12 by cam/spine interaction are effectively transferred through tibial insert 16, such that sliding motion will occur at interface 44 before any such sliding motion occurs at the interface between the proximal articular surfaces 56, 58 of tibial insert 16 and articular surface 22 of femoral component 12. Thus, the high surface congruence of the interface of interface of articular surface 22 of femoral component 12 and articulation surfaces 56, 58 of tibial insert 16 allows the above-described transverse forces to act as a motive force for sliding translation of both femoral component 12 and tibial insert 16 with respect to tibial component 14, rather than contributing to sliding motion between tibial insert 16 and femoral component 12.

It is contemplated that the specific frictional and geometric characteristics of proximal articular surfaces 56, 58 and distal bearing surface 62 of tibial insert 16 may be designed in a variety of ways, provided the interactions of adjacent components result in the above-described differential in resistance to facilitate initiation of sliding motion at interface 44 on application of a transverse force. Moreover, it is appreciated that frictional characteristics play a significant role in the resistance to sliding at both the proximal and distal faces of tibial insert 16. In order to ensure the proper differential in resistance to sliding, coefficients of friction at interface 44 and at the interface between the respective articular surfaces of tibial insert 16 and femoral component 12 should be chosen in view of the overall contact area between tibial insert 16 and the adjacent components, and in view of the pressures typically applied to knee prostheses. However, any compressive force applied to interface 44 is also necessarily applied to the interface between femoral component 12 and tibial insert 16. Thus, friction coefficients may be chosen such that the coefficient at interface 44 is lower than the coefficient at the femoral component/tibial insert interface. When the coefficients of friction are chosen in this way, sliding motion will reliably initiate at interface 44 for any typical amount of compressive force experienced in a human knee joint.

To facilitate such sliding translation in an anterior or posterior direction, tibial insert 16 includes oblong aperture 60 (FIG. 8) therethrough, which is disposed between medial and lateral articulation surfaces 56, 58. Aperture 60 is only slightly wider in the mediolateral direction than the corresponding mediolateral width of spine 18, which allows spine 18 to easily pass through aperture 60 when knee joint prosthesis 10 is assembled. However, the anteroposterior extent of aperture 60 (i.e., the "long" dimension of oblong aperture 60) is substantially larger than the corresponding anteroposterior span of spine 18. As discussed in detail below, oblong aperture 60 allows anterior and posterior sliding movement of tibial insert 16 (i.e., insert 16 is a "mobile bearing" insert), while substantially preventing medial or lateral movement.

2. Knee Joint Prosthesis Operational Characteristics

Referring generally to FIGS. 1-6, knee joint prosthesis 10 is shown in various positions starting from an extended configuration in which flexion has just begun (FIG. 1) through moderate and high degrees of flexion during a flexion motion (FIGS. 2 and 3), back through the moderate and high degrees of flexion during an extension motion (FIGS. 4 and 5), and back to the extended configuration after the extension motion (FIG. 6). As described below, the beginning of flexion of knee joint prosthesis 10 shifts knee joint prosthesis 10 from the configuration of FIG. 6 to the configuration of FIG. 1. Medial condyle 28 of femoral component 12 and medial articulation surface 56 of tibial component 14 are illustrated in FIGS. 1-6 for convenience, but it is of course-appreciated that similar interactions will occur between lateral condyle 30 and lateral articulation surface 58.

Referring specifically to FIG. 1, knee joint prosthesis 10 is shown in an extended configuration (i.e., zero degrees flexion) just after flexion has begun. The initial flexion of knee joint prosthesis 10 has begun to move posterior cam 36 toward spine 18 while moving anterior cam 34 away from spine 18. Thus, neither anterior cam 34 nor posterior cam 36 are in contact with anterior and posterior cam surfaces 52, 54 of proximal spine portion 50 at the early stage of flexion shown in FIG. 1. Anterior gap 64 exists between distal spine portion 46 and anterior surface 66 of oblong aperture 60 (FIG. 8) formed in tibial insert 16. As will be described in more detail below with respect to FIG. 6, anterior gap 64 results from an extension motion of knee joint prosthesis 10, such as the extension motion that would be required to bring knee joint prosthesis 10 to the extended configuration shown in FIG. 1.

Referring now to FIG. 2, knee joint prosthesis 10 is shown in a moderate-flexion configuration corresponding to approximately 45° of knee flexion, having undergone a flexion motion (represented schematically by arrow $F_1$ in FIG. 2) from the extended position in FIG. 1 to the partially flexed position shown in FIG. 2. Posterior cam 36 has engaged posterior cam surface 54 of proximal spine portion 50. As femoral component 12 articulates with respect to tibial insert 16 from extension (FIG. 1) toward mid-flexion (FIG. 2), posterior cam 36 and posterior cam surface 54 engage shortly after flexion begins and remain continuously engaged as flexion progresses (i.e., to the medium-flexion configuration of FIG. 2). This cam-spine engagement guides the motion of knee joint prosthesis 10, in that posterior cam 36 follows the profile of cam surface 54 (shown in FIG. 1 as a straight profile).

One aspect of the guidance provided by the interaction between posterior cam 36 and posterior cam surface 54 of proximal spine portion 50 is the movement of tibial insert 16 from the position shown in FIG. 1 to the position shown in FIG. 2. Specifically, tibial insert 16 moves posteriorly to close anterior gap 64 (FIG. 1) and open posterior gap 68 (FIG. 2) between spine 18 and posterior surface 70 of oblong aperture 60 (FIG. 8). This posterior movement results from the disparity in resistance to transverse forces at the proximal and distal surfaces of tibial insert 16, as discussed in detail above. More particularly, for a given proximal/distal compression applied to tibial insert 16 (e.g., along the longitudinal axis of the leg, such as from standing or walking), the transverse forces generated from interaction between articular surface 22 of femoral component 12 and articulation surfaces 56, 58 of tibial insert 16 are greater than the corresponding transverse forces from interaction between bearing surface 42 of tibial component 14 and distal surface 62 of tibial insert 16 (at interface 44). Thus, when posterior cam 36 first engages spine 18 during the early stages of flexion, femoral component 12 and tibial insert 16 move posteriorly, with the pair translating together as a single unit with respect to tibial component 14, as tibial insert 16 slides posteriorly with respect to tibial component 14 at interface 44. This posterior movement closes anterior gap 64 and opens posterior gap 68, as shown in FIG. 2.

Thus, the high conformity between articular surface 22 of femoral component 12 and articulation surfaces 56, 58 of tibial insert 16, particularly in the early stages of flexion, causes femoral component 12 and tibial insert 16 to move posteriorly as a unitary pair, so that interaction between posterior cam 36 and spine 18 causes anterior gap 64 to close and posterior gap 68 to open.

Turning now to FIG. 3, knee joint prosthesis 10 is shown after flexing further from the configuration shown in FIG. 2, to greater than 90° of flexion. During the flexion from about 45° (FIG. 2) to greater than 90° (represented schematically by arrow $F_2$ in FIG. 3), posterior cam 36 remains in engagement with posterior cam surface 54 of proximal spine portion 50. Further, posterior cam 36 moves distally along posterior cam surface 54, so that any curves or other geometries formed in posterior cam surface 54 will guide the motion profile of femoral component 12 during the flexion articulation.

In addition, anterior gap 64 was already closed at the partial flexion configuration shown in FIG. 2, so femoral component 12 ceased moving together with tibial insert 16 as a single unit. Instead, articular surface 22 of femoral component 12 began sliding over medial and lateral articulation surfaces 56, 58 to allow for femoral "roll-back". As a result of this sliding motion of femoral component 12, the point of contact between articular surface 22 and medial and lateral articulation surfaces 56, 58 of tibial insert 16 moved toward posterior side 26 of femoral component 12 as knee joint prosthesis 10 has gone from the partial flexion of FIG. 2 to the deep flexion of FIG. 3. However, the transverse, shear-based forces generated by this posterior movement of the point of contact are smaller than the corresponding forces which generated the movement of tibial insert 16 in the initial stages of flexion (as described above). This reduced shear force in deep flexion results from the contact between condyles 28, 30 and articulation surfaces 56, 58 gradually shifting from a relatively larger area of contact in an extension configuration (i.e., FIG. 1) to a relatively smaller area of contact in a flexion configuration (i.e., FIG. 3). The reduction in contact area is a result of a concomitant reduction in the radius of curvature of articular surface 22 of femoral component 12 toward posterior side 26, as illustrated schematically in FIGS. 1-6.

Turning now to FIG. 4, knee joint prosthesis 10 is shown in a deep flexion configuration, after cessation of the flexion motion represented by FIGS. 1-3 and during the initial stages of an extension motion (represented schematically by arrow $E_1$ in FIG. 4). For purposes of the present disclosure, such a change in the rotational direction of femoral component 12, e.g., from a flexion motion to an extension motion and vice-versa, is referred to as a prosthesis inflection. As shown in FIG. 4, posterior cam 36 disengages from posterior cam surface 54 of proximal spine portion 50 at the outset of the initial extension motion, and anterior cam 34 subsequently engages anterior cam surface 52 of proximal spine portion 50 as the initial extension motion continues.

After anterior cam 34 engages spine 18, posterior gap 68 begins to close and anterior gap 64 begins to reopen. Similar to the change from anterior gap 64 to posterior gap 68 discussed above, the change from posterior gap 68 to anterior gap 64 occurring during extension is the result of the femoral/insert shear forces having greater capacity to resist the transverse forces created by interaction between anterior cam 34 and spine 18, as compared to the corresponding transverse force resistance posed at interface 44. Specifically, the shear forces arising from interaction between articular surface 22 of femoral component 12 and articulation surfaces 56, 58 of tibial insert 16 are greater than the frictional interaction between tibial component 14 and tibial insert 16 at interface 44, so that tibial insert 16 "follows" femoral component 12 during anterior translation. Thus, femoral component 12 and tibial insert 16 translate anteriorly, with the pair translating as a single unit, as posterior gap 68 closes.

Turning now to FIG. 5, knee joint prosthesis 10 is shown at a partially flexed position, having undergone further extension (represented schematically by arrow $E_2$ in FIG. 5) from the deep flexion configuration shown in FIG. 4 to the partial flexion configuration shown in FIG. 5. Anterior cam 34 remains fully engaged with anterior cam surface 52 of proximal spine portion 50, and posterior gap 68 (FIG. 4) has closed completely to give way to a completely open anterior gap 64 (FIG. 5).

In addition, the nature of the interaction between anterior cam 34 and anterior cam surface 52 changes at different levels of flexion during an extension motion. In the illustrated embodiment, the relatively small surface contact between cam 34 and anterior cam surface 52, shown in FIG. 4, gives way to the relatively large corresponding surface contact therebetween shown in FIG. 5. In the illustrated embodiment of FIGS. 4-6, anterior cam 34 reaches a maximum area of engagement with anterior cam surface 52 at about 45° flexion when prosthesis 10 is moving from flexion to extension. This large surface contact may, for example, help drive a sliding motion between articular surface 22 and articulation surfaces 56, 58 (as discussed in detail below).

Moreover, the particular shape of anterior cam 34 and anterior cam surface 52 guides the articulation of femoral component 12 with respect to tibial insert 16 during extension motions. While the illustrated embodiment shows a particular cam/spine geometry which may be used to achieve desired motion guiding results, it is within the scope of the present disclosure that the shapes, sizes and geometries of anterior cam 34 and/or anterior cam surface 52 of proximal spine portion 50 may be altered to achieve any motion profile as required or desired for a particular application.

Turning now to FIG. 6, knee joint prosthesis 10 is shown in a fully extended position after having been extended (represented schematically by arrow $E_3$ in FIG. 6) from the position of deep flexion shown in FIG. 4, through the position of partial flexion shown in FIG. 5, and finally to the position of extension shown in FIG. 6. Anterior cam 34 remains in contact with anterior cam surface 52, and no contact between posterior cam 36 and posterior cam surface 54 of proximal spine portion 50 has occurred during the extension motion. Thus, anterior gap 64 remains fully open and posterior gap 68 (FIGS. 2-4) remain fully closed. If flexion begins again, femoral component 12 of knee joint prosthesis 10 will slide anteriorly to transition to the configuration shown in FIG. 1, and the process of flexion guidance resulting from the interaction of posterior cam 36 and spine 18 will once again take place as shown in FIGS. 1-3.

Advantageously, the "mobile bearing" design of tibial insert 16, i.e., the ability of tibial insert 16 to slide anteroposteriorly with respect to tibial component 14 at interface 44 to open or close anterior and posterior gaps 64, 68, allows anterior and posterior cams 34, 36 to engage with respective cam surfaces 52, 54 on proximal spine portion 50 of spine 18 throughout a wide range of motion in both flexion and extension. Thus, the motion profile of knee joint prosthesis 10 can be guided or influenced by an interaction between spine 18 and cams 34 or 36 of femoral component 12 throughout substantially the entirety of a flexion range of motion and substantially the entirety of an extension range of motion.

For example, in the exemplary illustrated embodiment, guided motion arising from cam/spine interaction may be achieved for up to 80° of extension motion (via interaction between anterior cam 34 and cam surface 52). Guided motion may be also be achieved for up to 95° of flexion motion or more (via interaction between posterior cam 36 and cam surface 54). In an exemplary embodiment, cam/spine interaction may occur from about 60° flexion to 155° flexion during a flexion motion, and from about 80° flexion to full extension (i.e., 0° flexion) during an extension motion.

Also advantageously, the guided motion in extension and flexion afforded by knee joint prosthesis 10 is achieved with minimal sliding motion at the articular interface between femoral component 12 and tibial insert 16. This minimization of sliding motion mitigates wear of medial and lateral articulation surfaces 56, 58 in at least two ways. First, the low amount of sliding motion minimizes the potential for friction-related wear. Second, the low amount of sliding motion allows for a high congruency between condyles 28, 30 and articulation surfaces 56, 58 (as discussed above), so that contact pressures therebetween, and the resulting forces experienced at the interface, are relatively low.

Also advantageously, various parameters of femoral component 12, tibial component 14, tibial insert 16 and spine 18 may be modified to achieve a particular, desired motion profile for both extension motions and flexion motions in knee joint prosthesis 10. These parameters include, for example: the shape and geometry of anterior and posterior cams 34, 36; the shape and geometry of anterior and posterior cam surfaces 52, 54; the size of proximal spine portion 50 of spine 18 and the relative location of attachment between spine 18 and tibial component 14; the overall size of oblong aperture 60 (and, by extension, the maximum sizes of anterior and posterior gaps 64, 68); the interaction characteristics between articular surface 22 of femoral component 12 and medial and/or lateral articulation surfaces 56, 58 of tibial insert 16 (i.e., shear force generation); the interaction characteristics between bearing surface 42 of tibial component 14 and distal surface 62 of tibial insert 16 at interface 44 (i.e., static and dynamic friction); and other characteristics of knee joint prosthesis 10 which may be altered according to any known methods.

While this invention has been described as having an exemplary design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

The invention claimed is:

1. A knee joint prosthesis, comprising:
   a tibial component implantable on a proximal tibia and having a proximally-facing tibial plate;
   a spine coupled to said tibial component and protruding proximally from said tibial plate, said spine defining an anteroposterior span;
   a tibial insert attachable to said tibial component, said tibial insert comprising:
      an insert bearing surface in abutting, sliding engagement with said tibial plate of said tibial component;
      a proximal articulation surface, said articulation surface positioned opposite said insert bearing surface; and
      an oblong aperture formed within said tibial insert so that at least a portion of said spine passes through said oblong aperture, said oblong aperture having an anteroposterior extent larger than said anteroposterior span of said spine, whereby said tibial insert is slidable in an anteroposterior direction with respect to said tibial component; and
   a femoral component implantable on a distal femur and articulable with said tibial insert between an extension configuration and a flexion configuration when said tibial component and said femoral component are implanted on the tibia and the femur, respectively, said femoral component comprising:
      an articular surface abutting said articulation surface of said tibial insert when said femoral component articulates with said tibial insert;
      an anterior cam engaged with said spine through a first range of motion from the flexion configuration to the extension configuration when said tibial component and said femoral component are implanted on the tibia and femur, respectively, said first range of motion including between 80 degrees flexion and zero degrees flexion; and
      a posterior cam engaged with said spine through a second range of motion from the extension configuration to the flexion configuration.

2. The knee joint prosthesis of claim 1, wherein the second range of motion is at least 95 degrees.

3. The knee joint prosthesis of claim 1, wherein the second range of motion extends from 155 degrees flexion to 60 degrees flexion.

4. A knee joint prosthesis movable between extension and flexion, said prosthesis comprising:
   a femoral component implantable on a distal femur and comprising:
      a lateral condyle and a medial condyle;
      an articular surface including respective surfaces of said lateral and medial condyles;
      a bone-contacting surface opposite said articular surface, said bone-contacting surface adapted to abut a distal portion of the femur when the femoral component is implanted on the femur;
      an anterior cam; and
      a posterior cam disposed posterior of said anterior cam;
   a tibial component implantable on a proximal tibia and having a tibial plate with a spine extending proximally therefrom, said anterior cam engaged with said spine when said tibial component and said femoral component are implanted on the tibia and the femur, respectively, to create a first transverse force as said femoral component is moved through a range of prosthesis motion from a flexion configuration to an extension configuration, said tibial plate defining a proximally-facing tibial component bearing surface; and a tibial insert comprising:

a distal insert bearing surface slidably abutting said tibial component bearing surface to define an interface therebetween, the interface providing a first resistance to transverse movement for a given compression between said tibial insert and said tibial component applied at said interface; and a proximal articular surface sized and shaped to abut said lateral condyle and said medial condyle of said femoral component to provide a second resistance to transverse movement for the given compression, the second resistance greater than the first resistance, said first transverse force greater than said first resistance to movement, whereby said femoral component and said tibial insert translate as a pair when said anterior cam engages said spine, and wherein, when a posteriorly-directed force acts on said femoral component with respect to said tibial component, said anterior cam engages said spine in a range of prosthesis motion including between 80 degrees flexion and zero degrees flexion.

5. The knee joint prosthesis of claim 4, wherein, when an anteriorly-directed force acts on the femoral component with respect to the tibial component, said posterior cam engages with said spine to create a second transverse force as said femoral component is moved from the extension configuration to the flexion configuration, said second transverse force greater than said first resistance to movement, whereby said femoral component and said tibial insert translate as a pair when said posterior cam engages said spine.

6. The knee joint prosthesis of claim 5, wherein said posterior cam engages said spine in a range of prosthesis motion between 60 degrees flexion and 155 degrees flexion.

7. The knee joint prosthesis of claim 4, wherein said posterior cam spans an intercondylar fossa formed between said medial condyle and said lateral condyle.

8. The knee joint prosthesis of claim 4, wherein said anterior cam is adjacent to an anterior end of an intercondylar fossa formed between said medial condyle and said lateral condyle.

9. The knee joint prosthesis of claim 4, wherein said anterior cam extends proximally from said bone-contacting surface of said femoral component.

10. The knee joint prosthesis of claim 4, wherein said tibial insert includes an oblong aperture defining an anteroposterior span that is greater than a corresponding anteroposterior span of said spine.

11. The knee joint prosthesis of claim 10, wherein said oblong aperture includes anterior and posterior walls, said spine engageable with said walls to define posterior and anterior limits of motion of said tibial insert.

12. The knee joint prosthesis of claim 11, wherein said first transverse force is greater than said second resistance to movement, whereby said femoral component is slidable with respect to said tibial insert when one of said posterior and anterior limits of motion is reached.

13. A knee joint prosthesis, comprising:

a femoral component implantable on a distal femur and comprising:

a lateral condyle and a medial condyle;

an articular surface including respective surfaces of said lateral and medial condyles;

a bone-contacting surface opposite said articular surface, said bone-contacting surface adapted to abut a distal portion of a femur when the femoral component is implanted on the femur;

an anterior cam; and a posterior cam disposed posterior of said anterior cam;

a tibial component implantable on a proximal tibia and having a tibial plate with a spine extending proximally therefrom, said tibial plate defining a proximally-facing tibial component bearing surface and said spine engages with said anterior cam and said posterior cam when said tibial component and said femoral component are implanted on the tibia and femur, respectively; and a tibial insert comprising:

a distal insert bearing surface slidably abutting said tibial component to define an interface therebetween, the interface providing a first resistance to transverse movement for a given compression between said tibial insert and said tibial component applied at said interface; and a proximal articular surface sized and shaped to abut said lateral condyle and said medial condyle of said femoral component to provide a second resistance to transverse movement for the given compression, the second resistance greater than the first resistance, wherein said spine disengages from one of said anterior cam and said posterior cam and engages with the other of said anterior cam and said posterior cam when a prosthesis inflection between extension and flexion movements occurs, and when a posteriorly-directed force acts on said femoral component with respect to said tibial component, said anterior cam engages said spine in a range of prosthesis motion including between 80 degrees flexion and zero degrees flexion.

14. The knee joint prosthesis of claim 13, wherein said articular surface of said femoral component cooperates with a proximal articulation surface of said tibial insert.

15. The knee joint prosthesis of claim 13, wherein, when an anteriorly-directed force acts on the femoral component with respect to the tibial component, said posterior cam engages said spine in a range of prosthesis motion between 60 degrees flexion and 155 degrees flexion.

16. The knee joint prosthesis of claim 13, wherein an oblong aperture formed in said tibial insert defines an anteroposterior span that is greater than a corresponding anteroposterior span of said spine.

17. The knee joint prosthesis of claim 13, wherein the spine is translationally fixed with respect to the tibial component.

* * * * *